(12) United States Patent
Ishida et al.

(10) Patent No.: US 7,789,830 B2
(45) Date of Patent: Sep. 7, 2010

(54) THROMBUS DETECTING APPARATUS, THROMBUS TREATING APPARATUS AND METHODS THEREFOR

(75) Inventors: Kazunari Ishida, Kashiwa (JP); Mikihiro Kaga, Abiko (JP); Naoto Fujita, Tachikawa (JP); Jun Kubota, Nagareyama (JP)

(73) Assignee: Hitachi Medical Corporation, Tokyo (JP)

( * ) Notice: Subject to any disclaimer, the term of this patent is extended or adjusted under 35 U.S.C. 154(b) by 918 days.

(21) Appl. No.: 10/579,208

(22) PCT Filed: Nov. 14, 2003

(86) PCT No.: PCT/JP03/14540

§ 371 (c)(1),
(2), (4) Date: Jan. 3, 2007

(87) PCT Pub. No.: WO2005/046482

PCT Pub. Date: May 26, 2005

(65) Prior Publication Data

US 2007/0213613 A1 Sep. 13, 2007

(51) Int. Cl.
*A61B 8/00* (2006.01)
(52) U.S. Cl. .................. 600/437; 600/407; 600/476; 600/478; 600/473
(58) Field of Classification Search .................. 600/437, 600/476, 478, 479, 481, 462, 463, 467
See application file for complete search history.

(56) References Cited

U.S. PATENT DOCUMENTS

| 5,305,745 | A | * | 4/1994 | Zacouto | ................ 600/324 |
| 5,307,816 | A | | 5/1994 | Hashimoto | |
| 5,348,015 | A | | 9/1994 | Moehring | |
| 5,441,051 | A | | 8/1995 | Hileman | |
| 5,502,651 | A | | 3/1996 | Jackson et al. | |
| 6,176,842 | B1 | * | 1/2001 | Tachibana et al. | ............ 604/22 |

(Continued)

FOREIGN PATENT DOCUMENTS

JP 3-49754 3/1991

(Continued)

*Primary Examiner*—Long V Le
*Assistant Examiner*—Joel F Brutus
(74) *Attorney, Agent, or Firm*—Antonelli, Terry, Stout & Kraus, LLP.

(57) ABSTRACT

A thrombus detecting apparatus provided with: a transducer (10), which is attached to a monitor portion of a subject and transmits and receives ultrasonic waves, a transmitter and receiver unit (11), which transmits and applies driving pulses to the transducer (10) and receives echo signals output from the transducer, and a detector (12) making use of ultrasonic waves, which processes output signals of the transmitter and receiver unit (11) and detects a thrombus passing through a blood vessel, and/or a light source (21), which generates living body inspection light, a probe (22), which is attached to a monitor portion of the subject and irradiates the living body inspection light from the light source (21) to the subject, a light receiving unit (25), which receives living body inspection light irradiated from the probe (22) and passed through the subject and outputs electrical signals depending on the intensity of the received living body inspection light, and a detector (26) making use of living body light, which processes the output signals of the light receiving unit (25) and detects a thrombus passing through a blood vessel.

16 Claims, 10 Drawing Sheets

U.S. PATENT DOCUMENTS

| | | | |
|---|---|---|---|
| 6,397,098 | B1 | 5/2002 | Uber, III et al. |
| 2002/0138003 | A1* | 9/2002 | Bukshpan .................. 600/443 |

FOREIGN PATENT DOCUMENTS

| JP | 3-146071 | 6/1991 |
|---|---|---|
| JP | 05-220152 | 8/1993 |
| JP | 9-262287 | 10/1997 |
| JP | 9-276352 | 10/1997 |
| JP | 2000-210300 | 8/2000 |
| JP | 2001-327495 | 11/2001 |
| JP | 2002-345787 | 12/2002 |
| JP | 2003-070787 | 3/2003 |
| JP | 2003-190170 | 7/2003 |
| JP | 2003-235846 | 8/2003 |
| WO | WO00/27288 | 5/2000 |
| WO | WO00/57793 | 10/2000 |
| WO | WO 00/57946 | 10/2000 |
| WO | WO 00/72756 | 12/2000 |
| WO | WO 02/45572 | 6/2002 |
| WO | WO 03/090599 | 11/2003 |

* cited by examiner

Fig. 10 ental units. Moreover, the detectors can be provided indi-
vidually for the respective detection units or can be provided
in common for the detection units. Still further, the detection
units can be designed to detect the thrombi through different
signal processings.

THROMBUS DETECTING APPARATUS, THROMBUS TREATING APPARATUS AND METHODS THEREFOR

FIELD OF THE INVENTION

The present invention relates to a thrombus detecting apparatus, which detects a thrombus (a mass of blood) flowing through a blood vessel in a living body, a thrombus treating apparatus, which dissolves and removes the thrombus detected by the thrombus detecting apparatus and methods therefor.

BACKGROUND ART

Since a thrombus induced in a blood vessel in a living body causes to lose fluidity of blood, disturbs blood stream and plugs the blood vessel, the thrombus is one cause for diseases such as vasculopathy. It is said that brain infarction, which is one brain vasculopathy, is primarily caused through embolization of a blood vessel in a brain by a thrombus.

Accordingly, it is understood that an onset of diseases can be suppressed by detecting the thrombus in the blood vessel and by removing the same. For this purpose, JP-A-2001-327495 proposes an ultrasonic wave device, which is constituted so as to specify a thrombus (embolization) portion in a brain blood vessel by making use of an image taking ultrasonic wave device and to perform treatment by irradiating treatment use ultrasonic wave to the thrombus (embolization) portion to dissolve the same. In the ultrasonic wave device disclosed in the document, such as position and size of the thrombus (embolization) portion induced in the brain blood vessel are grasped by making use of the image taking use ultrasonic waves, and the dissolve treatment use ultrasonic waves are accurately irradiated to the thrombus (embolization) portion.

Now, the brain infarction includes such as lacuna infarction, atheroma thrombus infarction and cardiogenic cerebral embolism. The lacuna infarction is one, in which a fine artery in a brain is damaged due to high blood pressure and plugged thereby to form a small infarction nest at a deep portion in the brain. The atheroma thrombus infarction is one, which is caused by narrowing such as an artery at the neck and a comparatively large artery in the skull due to hardening (atheroma hardening) the artery where a thrombus is induced to plug the same completely or the thrombus thus induced peels off and flows out to plug the downstream thereof. The cardiogenic cerebral embolism is one, which is caused when a thrombus induced in a heart is peeled off and flows into an artery in the brain. Further, a cause for vasculopathy can be induced after when an operation such as in obstetrics and gynecology field and in hypogastrium and pelvic, a thrombus is induced and a part of the thrombus is peeled off and flows into an artery.

In the ultrasonic wave device as disclosed in the above referred to JP-A-2001-327495, although it is possible to observe the embolization portion already formed in a blood vessel and to treat the same, it is impossible to find out in advance a thrombus flowing through a blood vessel, which will be a cause for disease and to dissolve and remove the same.

An object of the present invention is to provide a thrombus detecting apparatus, which permits to detect a thrombus, a possible cause of disease, flowing through a blood vessel and a method therefor.

Another object of the present invention is to provide a thrombus treating apparatus, which permits to detect a thrombus, a possible cause of disease, flowing through a blood vessel and to dissolve and remove the same and a method therefor.

SUMMARY OF THE INVENTION

A thrombus detecting apparatus according to the present invention is provided with transducers, which transmit and receive ultrasonic waves, a transmitter and receiver unit, which transmits and applies driving pulses to the transducers and receives echo signals output from the transducers and a detector making use of ultrasonic waves, which processes output signals of the transmitter and receiver unit and detects a thrombus passing through a blood vessel, and/or a light source, which generates living body inspection light, a light receiving unit, which receives the living body inspection light generated from the light source and passed through a subject and outputs electrical signals depending on the intensity of the received living body inspection light and a detector making use of living body light, which processes output signals of the light receiving unit and detects a thrombus passing through a blood vessel.

The transducers are disposed near a blood vessel to be monitored and from which ultrasonic waves are transmitted and echo signals are received. In a case of a normal blood vessel where no thrombi exist, only a waveform is observed in which the echo signals are reflected at positions of the respective inner walls of the blood vessel (normal waveform). On the contrary, in a case when a thrombus is passing through a blood vessel, in association with the thrombus passing another reflection waveform depending on the size of the thrombus is observed between the two reflection waves in addition to the waveform in which the echo signals are reflected at positions of the respective inner walls of the blood vessel. The detection unit making use of ultrasonic waves detects the reflection waveform depending on the size of the thrombus.

Probes for the light source are disposed near a blood vessel, from which living body inspection light is irradiated and the light receiving unit receives the living body inspection light passed through inside the blood vessel and converts the same into electrical signals. In a case of a normal blood vessel where no thrombi exist, only a flat waveform is observed in which no amplitude of the electrical signals varies. On the contrary, in a case when a thrombus is passing through a blood vessel, in association with the thrombus passing a part of the irradiated living body inspection light is absorbed and the detected electrical signals show a waveform of which amplitude temporarily decreases. The detection unit making use of the living body light detects that a thrombus has passed when the electrical signals decrease.

When combining the detection unit making use of ultrasonic waves and the detection unit making use of the living body light, both advantages can be taken that the detection unit making use of ultrasonic waves shows a high detection sensitivity at a deep portion in the skin and the detection unit making use of the living body light shows a high detection sensitivity at a shallow portion in the skin, thereby the thrombus passing can be detected with a high accuracy.

Further, when a passing of a thrombus having a larger size more than a predetermined size is detected by the detection unit or when a number of detections of thrombi having a larger size more than a predetermined size is exceeded over a predetermined number, an alarm device alarms the fact by making use of such as sound and image display. Further, the alarm device can be designed in such a manner that the alarm device sets individual alarm levels for the respective detection results of the detection unit making use of ultrasonic waves and the detection unit making use of the living body light and generates individual alarms when the respective alarm levels are reached or alternatively, while correlating the respective detection results of the detection unit making use of ultrasonic waves and the detection unit making use of the living body light, the alarm device generates an alarm when both detection results reach the respective alarm levels.

Further, another feature of the present invention is that the thrombus detecting apparatus is provided with a portable self-power source. Thereby, the subject can carry the thrombus detecting apparatus and can monitors and detects generation of a thrombus at any time and any place.

Further, in the present invention, the thrombus detecting apparatus is provided with a treatment use ultrasonic wave generating apparatus, which transmits ultrasonic waves for dissolving a thrombus flowing in a blood vessel based on the detection result of the detection unit, thereby, when a thrombus is detected, the thrombus dissolving use ultrasonic waves are irradiated immediately for dissolving the thrombus. Thus, the treatment can be performed in early time by dissolving and removing the thrombus detected.

Further, in the thrombus treating apparatus, the alarm device, which is a constitutional element for the thrombus detecting apparatus, is an optional device, and when a thrombus is detected the thrombus dissolving use ultrasonic waves are immediately irradiated from the treatment use ultrasonic wave generation apparatus. Further, in place of the alarm device, a display device, which displays the operation of the treatment use ultrasonic wave generation apparatus, can be added.

Further, the thrombus treating apparatus is provided with a portable self-power source. Thereby, the subject can carry the thrombus treating apparatus and can monitors and detects generation of a thrombus at any time and any place and can treats in early time by dissolving and removing the thrombus.

Further, in order to prevent a condition where a thrombus plugs a blood vessel and disturbs blood flow, the thrombus treating apparatus is provided with a living body light measurement apparatus and an injection device and through the use of the injection device a thrombus dissolving agent is injected to a subject depending on the blood stream condition observed by the living body light measurement apparatus.

Further, the thrombus treating apparatus is provided with a means which monitors the injection amount of the thrombus dissolving agent by the injection device and the irradiation time of the ultrasonic waves by the treatment use ultrasonic wave generation apparatus and adjusts and controls the injection amount and the irradiation time. Since it is sometimes dangerous for a patient when a large amount of the thrombus dissolving agent is injected or the thrombus dissolving use ultrasonic waves are irradiated for a long time, through the provision of the adjustment and control means the injection amount and the irradiation time are managed.

Further, the thrombus treating apparatus is provided with a thrombus dissolving agent activating use ultrasonic wave generating apparatus, which transmits ultrasonic waves to the thrombus dissolving agent for activating the thrombus dissolving agent injected into the blood vessel from the injection device, with which the effect of the injected thrombus dissolving agent can be further enhanced.

With the thrombus detecting apparatus according to the present invention, a thrombus, a possible cause of disease, flowing in the blood vessel can be detected without delay. With the thrombus treating apparatus according to the present invention, a thrombus, a possible cause of disease, flowing in the blood vessel can be detected without delay and can be dissolved and removed.

DESCRIPTION OF BEST MODES FOR CARRYING OUT THE INVENTION

Herein below, embodiments of the present invention will be explained with reference to the drawings attached.

Figure 1:
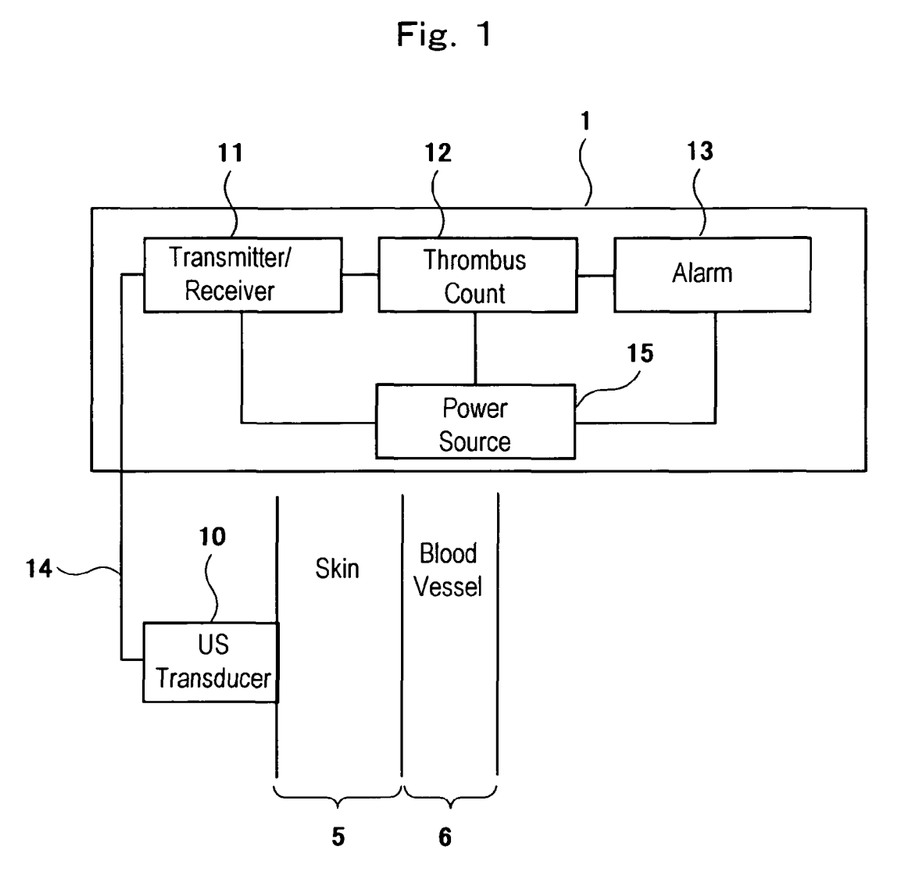
FIG. 1 is a diagram showing a first embodiment relating to a thrombus detecting apparatus according to the present invention.

FIG. 1 is a diagram showing a first embodiment relating to a thrombus detecting apparatus according to the present invention. The thrombus detecting apparatus is designed to detect number of thrombi having a size larger than a predetermined one flowing through a blood vessel by making use of ultrasonic waves and includes an ultrasonic wave transducer 10, a transmitter and receiver unit 11, a thrombus counting unit 12, an alarm device 13 and a power source 15 therefor, wherein the transmitter and receiver unit 11, the thrombus counting unit 12, the alarm device 13 and the power source 15 are provided in the main body side of the thrombus detecting apparatus 1 and the ultrasonic wave transducer 10 is led out from the thrombus detecting apparatus 1 via a cable 14.

The ultrasonic wave transducer 10 is an ultrasonic wave probe used such as in an ordinary ultrasonic wave diagnosis apparatus, and which generates ultrasonic waves by converting pulse like electrical signals into mechanical vibrations and further converts mechanical vibrations due to reflection echoes from a subject into pulse like electrical signals. The ultrasonic waves generated from the ultrasonic wave transducer 10 are set to be concentrated to a blood vessel 6 representing a predetermined focusing position via a skin 5 of the subject. The transmitter and receiver unit 11 generates pulse signals for driving the ultrasonic wave transducer 10 and transmits the same as well as amplifies weak echo signals output from the ultrasonic wave transducer 10, which is vibrated by the ultrasonic waves reflected from the inside of the subject and outputs the same to the thrombus counting unit 12. The thrombus counting unit 12 detects thrombi having a size larger than a predetermined size passed through the blood vessel 6 based on the amplified echo signals, counts the detected number and outputs the count value to the alarm device 13. Such as when the thrombus counting unit 12 detects passing of a thrombus and when the count value reaches more than a predetermined number, the alarm device 13 informs to the user of the thrombus detecting apparatus as an alarm such as by displaying the fact and by generating a sound.

Figure 2:
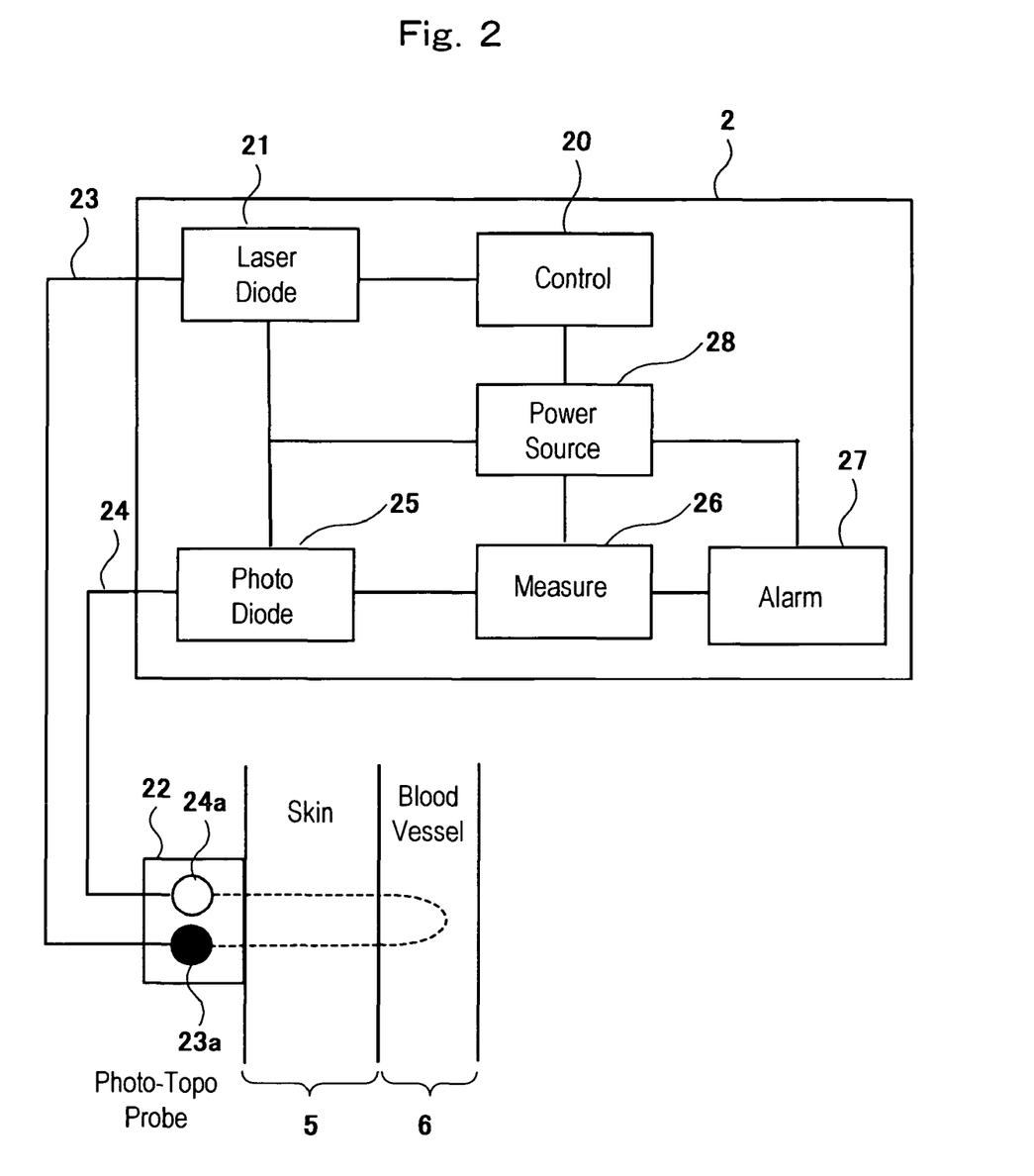
FIG. 2 is a diagram showing a second embodiment relating to a thrombus detecting apparatus according to the present invention.

FIG. 2 is a diagram showing a second embodiment relating to a thrombus detecting apparatus according to the present invention. The thrombus detecting apparatus is designed to detect thrombus having a size larger than a predetermined size or number thereof flowing through a blood vessel by making use of a living body light measurement apparatus, which receives light passed through a living body and measures conditions inside the living body and is constituted by a control unit 20, a laser diode 21, a living body light measurement probe 22, an irradiation light optical fiber 23, a detection light optical fiber 24, a photo diode 25, a measurement unit 26, an alarm device 27, and a power source 27 therefor. The control unit 20, the laser diode 21, the photo diode 25, the measurement unit 26, the alarm device 27 and the power source 28 are provided in the main body side of the thrombus detecting apparatus 2 and the living body light measurement probe 22 is led out from the thrombus detecting apparatus 2 via the irradiation light optical fiber 23 and the detection light optical fiber 24.

The living body light measurement probe 22 includes a light emitting top end 23a of the irradiation light optical fiber 23 and a light receiving top end 24a of the detection light optical fiber 24. The control unit 20 outputs driving signals to the laser diode 21 for outputting from the laser diode 21 two light having different measurement wavelength, for example two near infrared light having wavelength of 780 nm and 830 nm. The laser diode 21 outputs the light having the wavelength corresponding to the driving signals to the irradiation light optical fiber 23. Thereby, the light is emitted from the light emitting top end 23a in the living body light measurement probe 22. The emitted light passes the skin 5 and the blood vessel 6 of the subject and enters to the light receiving top end 24a in the living body light measurement probe 22 as living body inspection light. The detection light optical fiber 24 guides the entered light from the light receiving top end 24a to a light receiving face of the photo diode 25. The photo diode 25 receives the living body inspection light passed through the skin 5 and the blood vessel 6 of the subject and outputs electrical signals depending on the intensity of the received living body inspection light to the measurement unit 26. The measurement unit 26 detects a thrombus having a size larger than a predetermined size passed inside the blood vessel 6 based on the electrical signals output from the photo diode 25, counts number of detection and outputs the count value to the alarm device 27. When the count value from the measurement unit 26 reaches more than a predetermined number, the alarm device 27 informs to the user of the thrombus detecting apparatus as an alarm such as by displaying the fact and by generating a sound.

Figure 3:
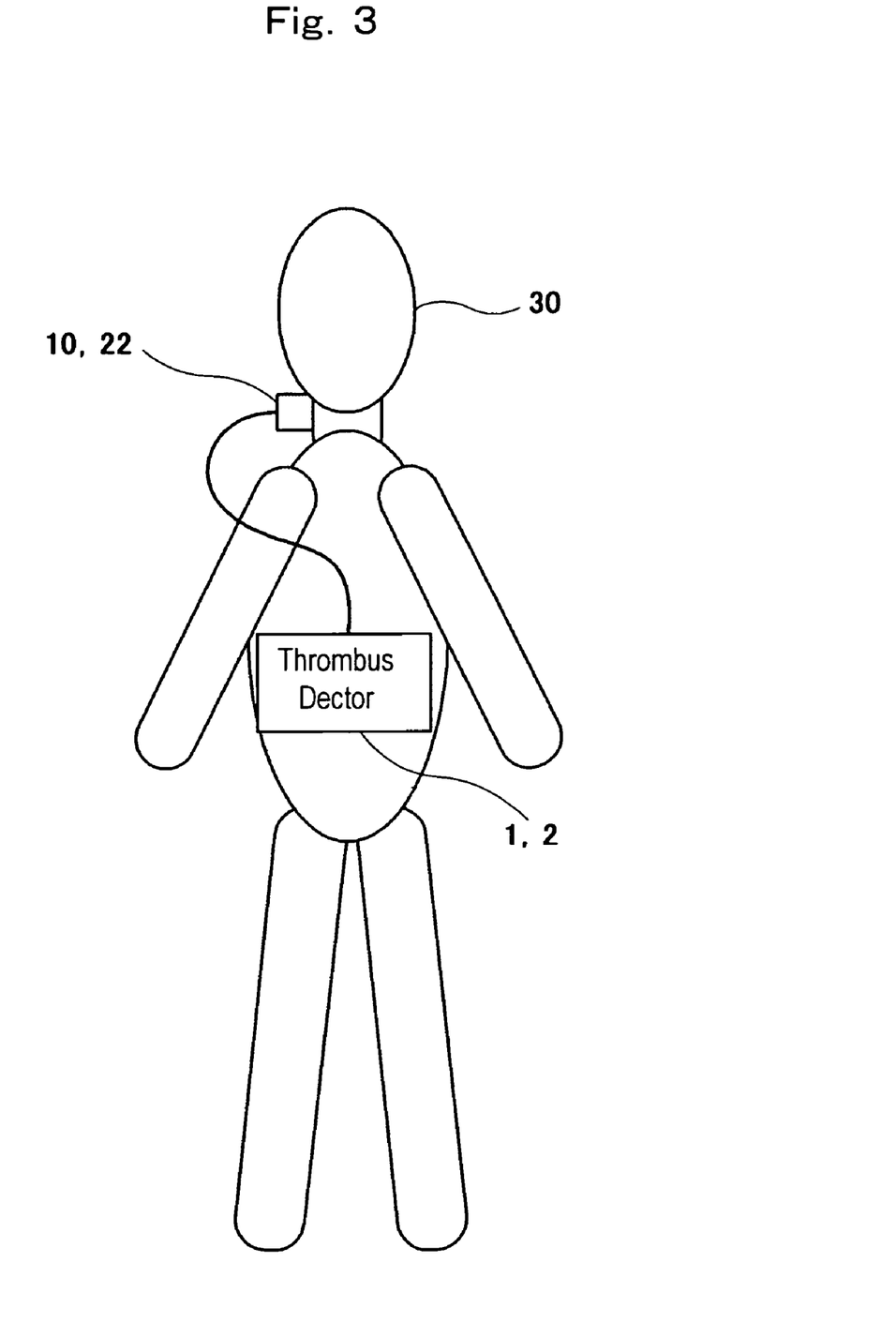
FIG. 3 is a diagram showing an attached condition of the thrombus detecting apparatus as shown in FIG. 1 and FIG. 2 on a user.

FIG. 3 is a diagram showing an attached condition of the thrombus detecting apparatus as explained in FIG. 1 and FIG. 2 on a user. The size of the thrombus detecting apparatus is about what a human body 30 can always carry as shown in the drawing. In the drawing, the human body 30 carries the thrombus detecting apparatus 1 or 2, the ultrasonic wave transducer 10 or the living body light measurement probe 30 is attached on the skin near a blood vessel at the scruff of the neck and prepares to detect a thrombus having a size larger than a predetermined size flowing through the blood vessel. Thereby, the human body can perform such as other works and spend an ordinary life while carrying the thrombus detecting apparatus. Further when the detection number of thrombi exceeds the predetermined number and an alarm is generated, the user can hurry to a near by hospital or it's regular hospital. Further, although not illustrated, a system can be built in which before attaching the apparatus on the user, a doctor sets a notification level of the user depending on the state of the disease and when the thrombus detecting apparatus generates an alarm, the alarm is notified to a medical institution such as it's regular hospital or to a fire department for calling an ambulance via a wireless line (such as cell phone communication network).

Figure 4:
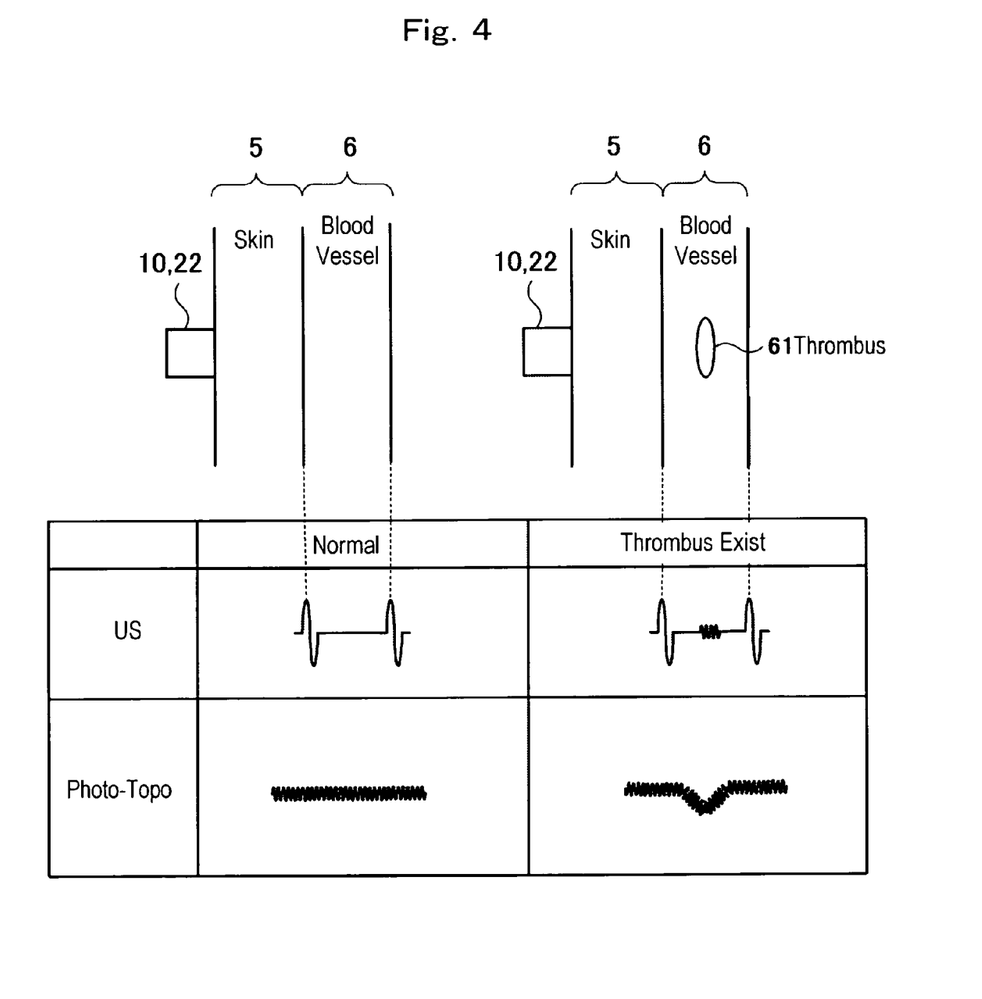
FIG. 4 is a diagram for explaining the operation of the thrombus detecting apparatus as shown in FIG. 1 and FIG. 2.

FIG. 4 is a diagram for explaining the operation of the thrombus detecting apparatus as shown in FIG. 1 and FIG. 2. In FIG. 4, "ultrasonic wave" at the upper column, a waveform of echo signals detected by the thrombus detecting apparatus 1 as shown in FIG. 1, "living body light" at the lower column, a waveform of electrical signals detected by the thrombus detecting apparatus 2 as shown in FIG. 2, "normal" at the left side column, exemplary signals of a normal blood vessel when no thrombus 61 exists and "thrombus exist" at the right side column, exemplary signals when a thrombus 61 has passed through the blood vessel 61 are respectively shown. As will be apparent from the drawing, in a case of a normal blood vessel in which no thrombus exists, the echo signals show a waveform in which the echo signals are reflected at positions of the respective inner wall portions of the blood vessel 6 and the electrical signals of the penetrating living body light show a flat waveform with no amplitude variation. On the contrary, in a case when a thrombus 61 is passing through a blood vessel 6, in association with the thrombus 61 passing, the echo signals show another waveform depending on the size occupied by the thrombus 61 between the two waves in addition to the waveform (normal waveform) in which the echo signals are reflected at positions of the respective inner walls of the blood vessel and the electrical signals of the penetrating living body light show a waveform of which amplitude temporarily decreases due to partial absorption of the penetrating living body inspection light by the thrombus. The thrombus counting unit 12 or the measurement unit 26 detects that a thrombus has passed through the blood vessel 6 based on such signal variation and determines the number of such thrombus passing.

Figure 5:
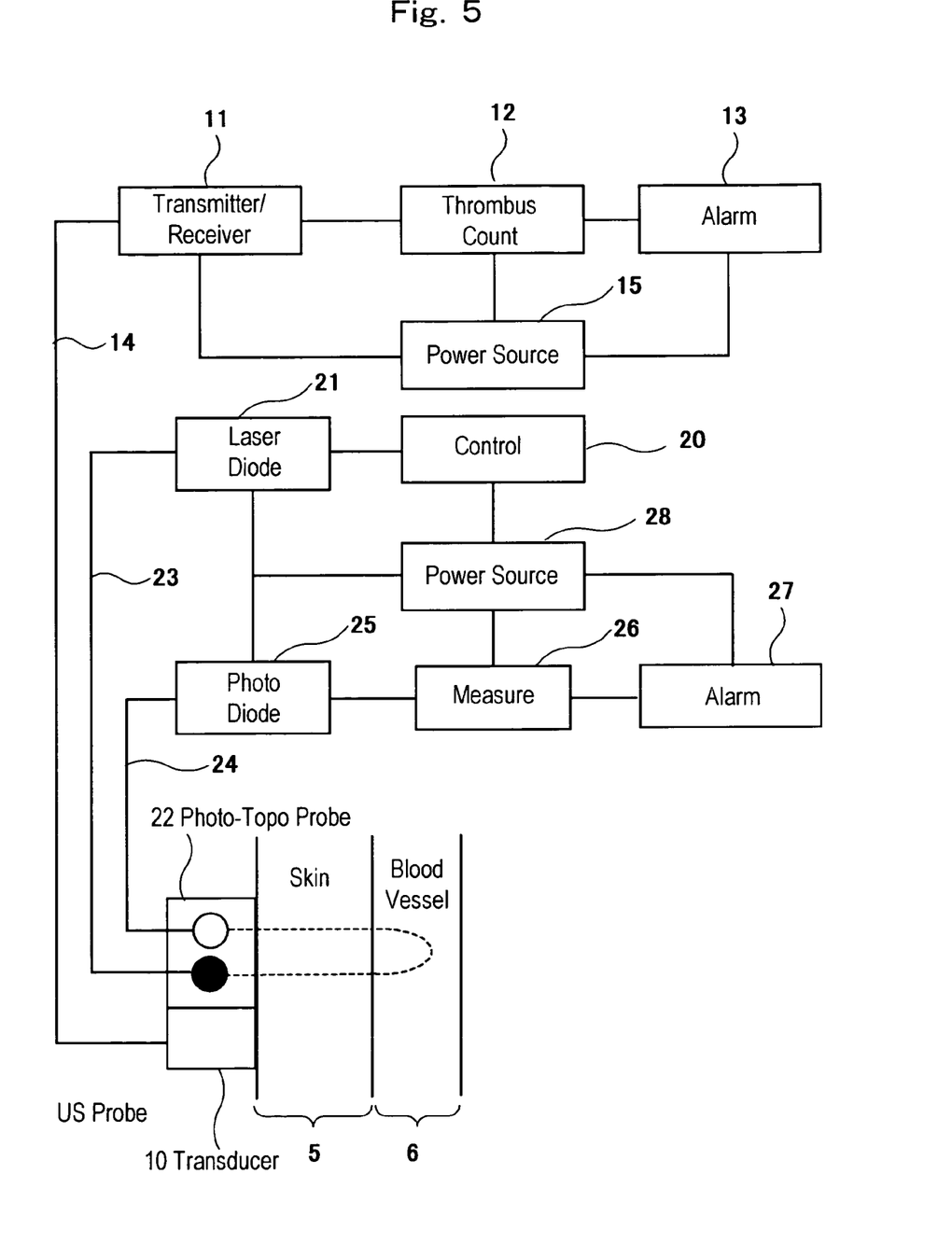
FIG. 5 is a diagram showing a third embodiment relating to a thrombus detecting apparatus according to the present invention.

FIG. 5 is a diagram showing a third embodiment relating to a thrombus detecting apparatus according to the present invention. FIG. 5 thrombus detecting apparatus is a combination of FIG. 1 thrombus detecting apparatus 1 making use of ultrasonic waves and FIG. 2 thrombus detecting apparatus 2 making use of living body light. In FIG. 5, since the same reference numerals are assigned to the same constituents as in FIGS. 1 and 2, the explanation thereof is omitted. As shown in FIG. 5, through combining both, the different features of the detection sensitivity of both depending on the depth from the skin are advantageously utilized and a thrombus passing can be detected with a high accuracy.

Namely, with the measurement making use of living body light, the measurement depth is about 20 mm, with the measurement making use of ultrasonic waves the measurement depth is about from 20 mm to 240 mm, therefore, both measurements are used differently, in that when measuring a blood vessel at a deep portion the measurement making use of ultrasonic waves is used and when measuring a blood vessel at a shallow portion the measurement making use of living body light is used.

Figure 6:
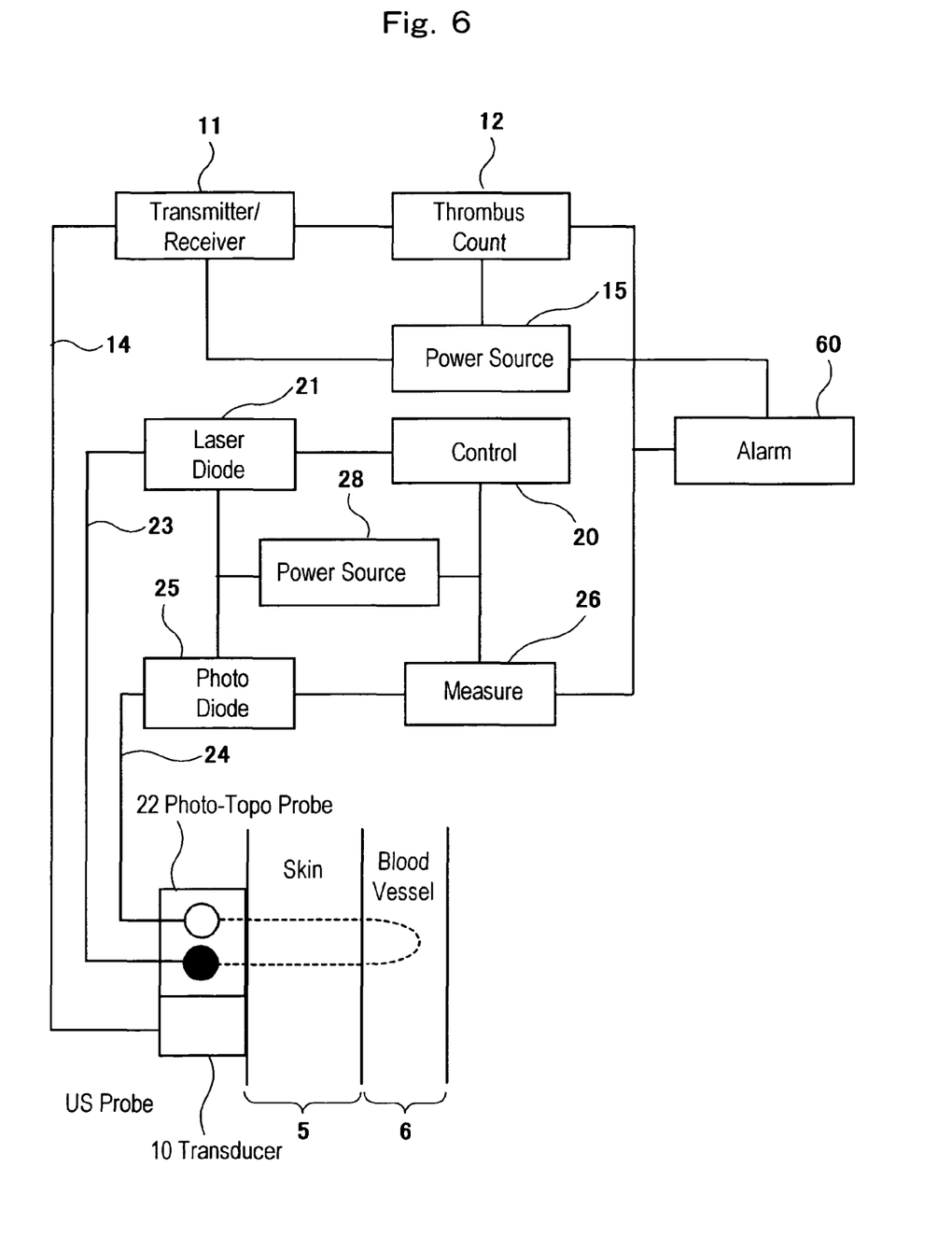
FIG. 6 is a diagram showing a fourth embodiment relating to a thrombus detecting apparatus according to the present invention.

FIG. 6 is a diagram showing a fourth embodiment relating to a thrombus detecting apparatus according to the present invention. FIG. 6 thrombus detecting apparatus is a combination of FIG. 1 thrombus detecting apparatus 1 making use of ultrasonic waves and FIG. 2 thrombus detecting apparatus 2 making use of living body light, and a different point from FIG. 5 is that the alarm devices 13 and 27 in FIG. 5 are constituted by a single common alarm device 60. Although the alarm devices 13 and 27 in FIG. 5 are constituted so as to operate separately, the alarm device 60 of the present embodiment is constituted so as to generate an alarm based on a counted value from the thrombus counting unit 12 and the measurement unit 26. For example, the alarm device 60 generates an alarm when both counted values from the thrombus counting unit 12 and the measurement unit 26 exceed a predetermined value. Further, when one of the counted values exceeds the predetermined value and the other is slightly below the predetermined value, it is possible to design to permit to generate an alarm. Further, the predetermined count values can be determined differently for the thrombus counting unit 12 and the measurement unit 26.

Figure 7:
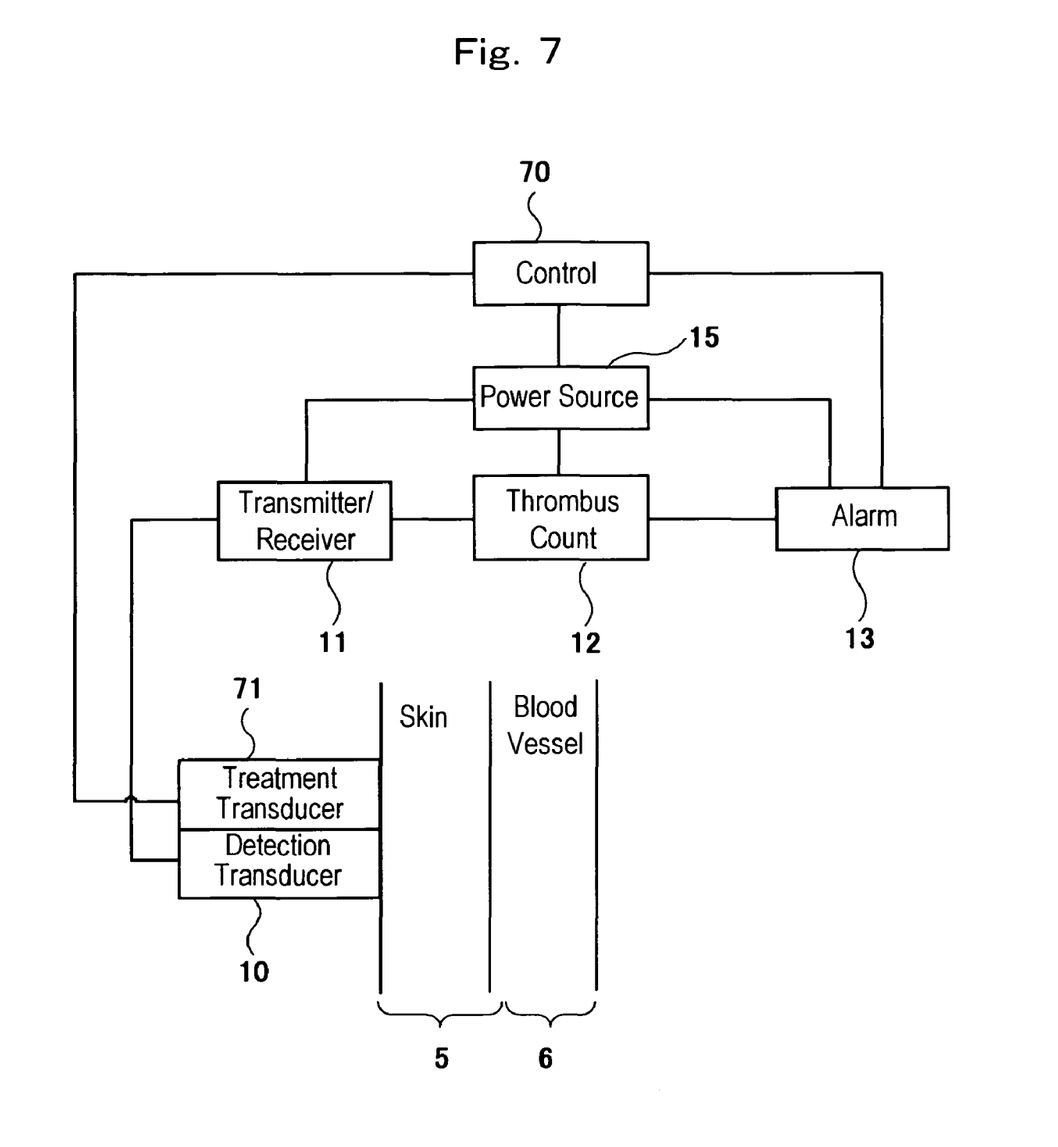
FIG. 7 is a diagram showing a first embodiment relating to a thrombus treating apparatus according to the present invention.

FIG. 7 is a diagram showing a first embodiment relating to a thrombus treating apparatus according to the present invention. In FIG. 7, since the same reference numerals are assigned to the same constituents as in FIG. 1, the explanation thereof is omitted. The thrombus treating apparatus as shown in FIG. 7 is one in which a treatment use transducer 71 and a control unit 70 are added to the thrombus detecting apparatus as shown in FIG. 1. The control unit 70 supplies to the treatment use transducer 71 drive pulses having frequency of 100~500 [kHz] and intensity of 0.5~1.5 [W/cm$^2$] in response to a signal from the alarm generating device 13. Further, the drive pulses supplied to the detection use transducer 10 have a frequency of 3 [kHz] and intensity of about 1/10 of the above. However, these numeral values are only an example and values other than the above can of course be used. Although the alarm device 13 generates an alarm when the count value from the thrombus counting unit 12 exceeds the predetermined value, in the present embodiment, the signal to the control unit 70 is designed to be output every time when the count value from the thrombus counting unit 12 is input to the alarm device 13. Further, the count value from the thrombus counting unit 12 can be directly input to the control unit 70 and based on the input the control unit 70 can output the drive pulses to the treatment use transducer 71. In this instance, the alarm device 13 can be omitted.

Figure 8:
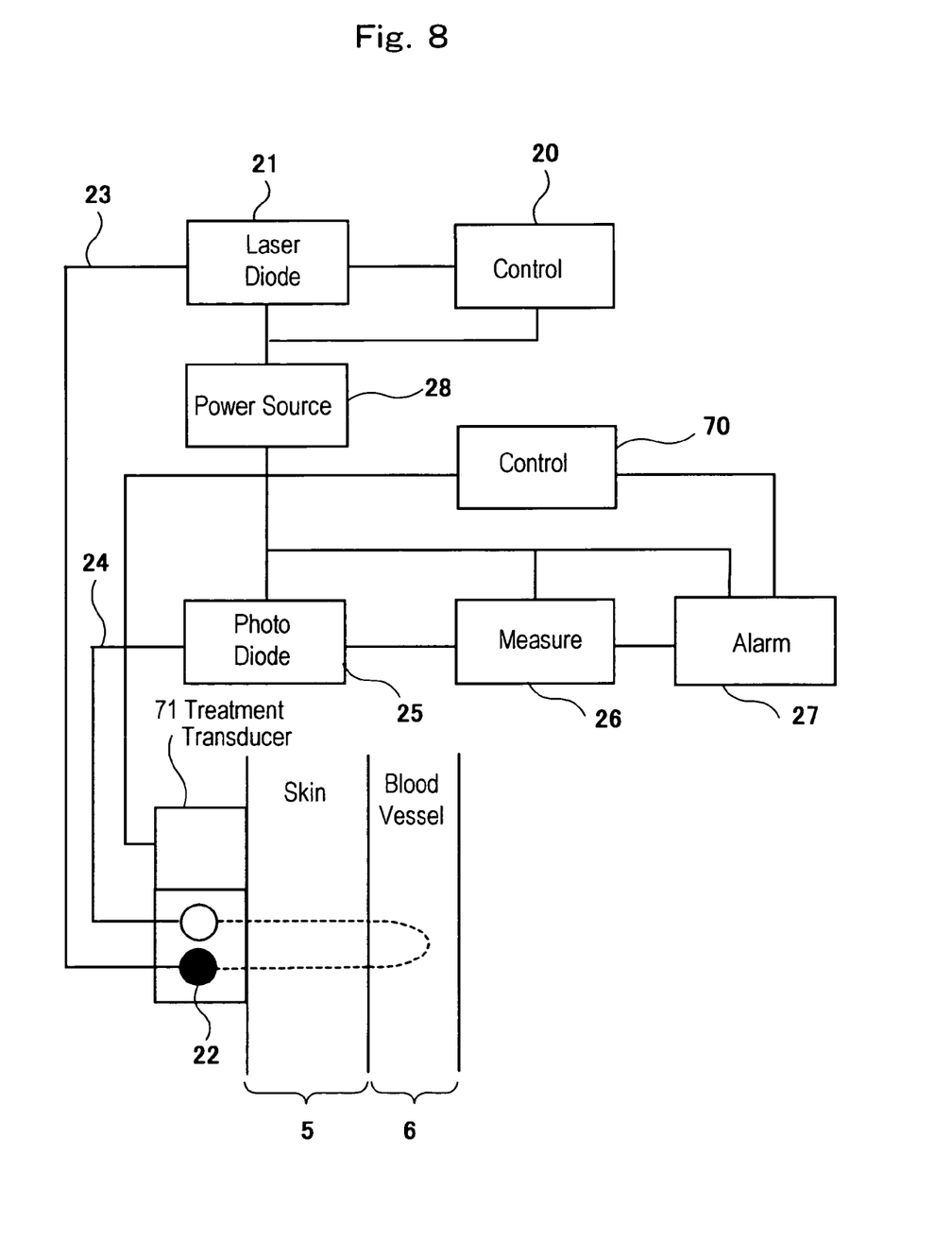
FIG. 8 is a diagram showing a second embodiment relating to a thrombus treating apparatus according to the present invention.

FIG. 8 is a diagram showing a second embodiment relating to a thrombus treating apparatus according to the present invention. In FIG. 8, since the same reference numerals are assigned to the same constituents as in FIGS. 2 and 7, the explanation thereof is omitted. The thrombus treating apparatus as shown in FIG. 8 is one in which a treatment use transducer 71 is added to the thrombus detecting apparatus as shown in FIG. 2. The control unit 70 supplies to the treatment use transducer 71 drive pulses having frequency of 100~500 [kHz] and intensity of 0.5~1.5 [W/cm$^2$] in response to a signal from the alarm device 27. Although the alarm device 27 generates an alarm when the count value from the measurement unit 26 exceeds the predetermined value, in the present embodiment too, the signal to the control unit 70 is designed to be output every time when the count value from the measurement unit 26 is input to the alarm device 27. Further, the count value from the measurement unit 26 can be directly input to the control unit 70 and based on the input the control unit 70 can output the drive pulses to the treatment use transducer 71. In this instance, the alarm device 27 can be omitted. In FIGS. 7 and 8 embodiments, although an example of adding the treatment use ultrasonic wave transducer to the FIGS. 1 and 2 thrombus detecting apparatus is explained, like treatment use transducer can be added to FIGS. 5 and 6 thrombus detecting apparatus.

Figure 9:
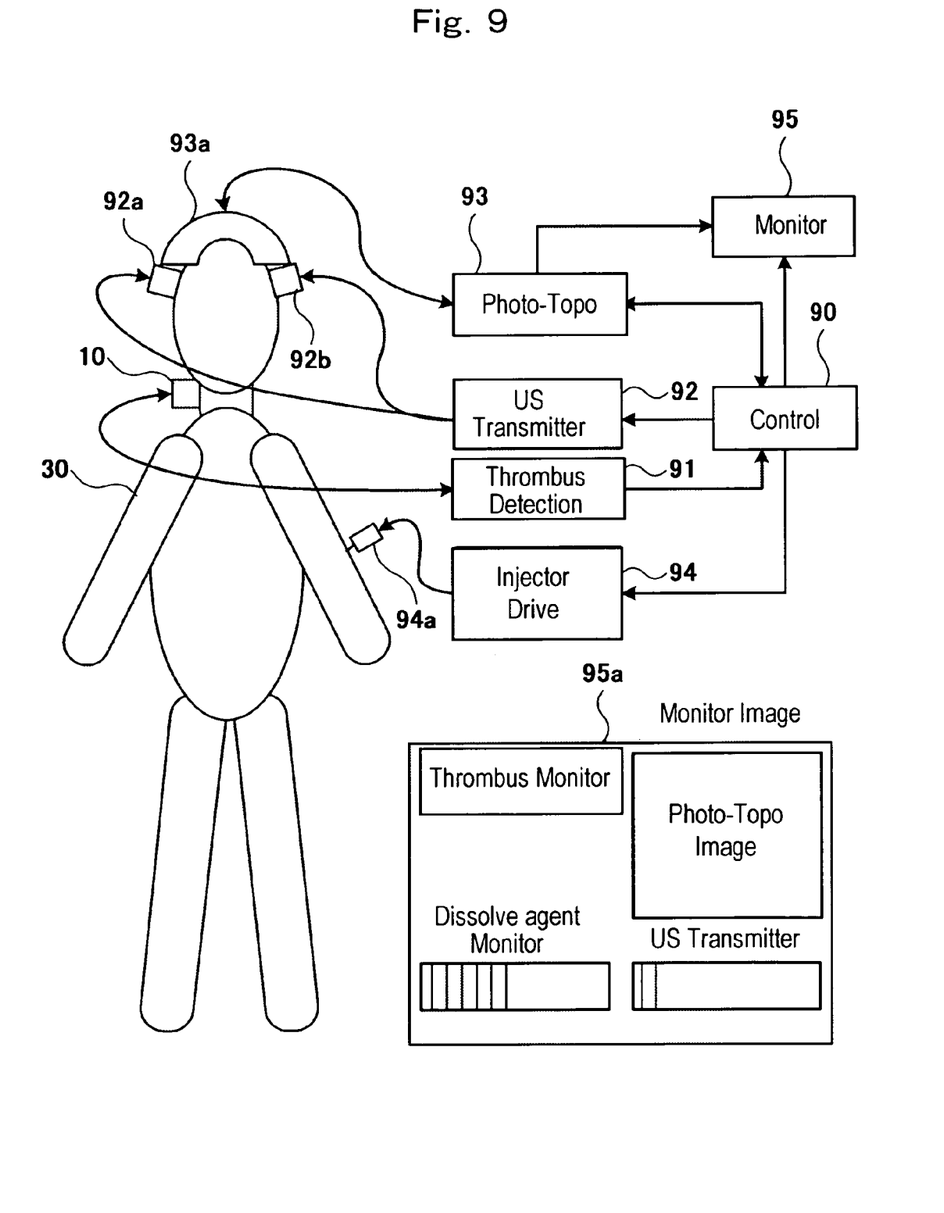
FIG. 9 is a diagram showing a third embodiment relating to a thrombus treating apparatus according to the present invention.

FIG. 9 is a diagram showing a third embodiment relating to a thrombus treating apparatus according to the present invention. Since the thrombus treating apparatus as shown in FIGS. 7 and 8 are one in which the treatment use ultrasonic wave transducer is added to the potable thrombus detecting apparatus as shown in FIGS. 1 and 2, the thrombus treating apparatus as shown in FIGS. 7 and 8 are of course portable. On the other hand, since FIG. 9 thrombus treating apparatus is one used in a medical facility such as a hospital, in addition to FIGS. 1 and 2 thrombus detecting apparatus a treatment use ultrasonic wave transducer, a thrombus dissolving agent injection device as well as a living body light measurement apparatus are provided. A control unit 90 is for controlling the entirety of FIG. 9 thrombus treating apparatus. The operation of the control unit 90 will be explained together with the respective constitutional elements.

A thrombus detection unit 91 is constituted by the transmitter and receiver unit 11 and the thrombus counting unit 12 as shown in FIG. 1, detects a thrombus flowing through a blood vessel by making use of the detection use transducer 10 attached to the skin nearest to a blood vessel at the scruff of the neck of the human body 30 and outputs the detection signals to the control unit 90. The control unit 90 senses that a thrombus is passing through the blood vessel based on the detection signals output from the thrombus detection unit 91 and outputs a thrombus treatment starting signal to a ultrasonic wave transmission unit 92. Further, in place of the thrombus detection unit 91 and the detection use transducer 10, the thrombus detecting apparatus 2 and the living body light measurement probe 22 as shown in FIG. 2 can be used.

The ultrasonic wave transmission unit 92 supplies drive pulses to treatment use transducers 92a and 92b in response to the input of the thrombus treatment starting signal from the control unit 90. The treatment use transducers 92a and 92b are attached to a head portion of the human body 30 and irradiates thrombus dissolving use ultrasonic waves to the head portion of the human body 30 in response to the drive pulses from the ultrasonic wave transmission unit 92 as well as irradiates ultrasonic waves for activating the thrombus dissolving agent to a blood vessel of the human body 30 which will be explained later.

A living body light measurement apparatus 93 irradiates two light having different wavelength, for example, two near infrared light having wavelength of 780 nm and 830 nm after modulating the same with different plural frequencies into the head portion by making use of a probe 93c attached to the head portion of the human body 30, receives respective living body inspection light having the two wavelengths irradiated and passed inside the head portion, produces two electrical signals depending on the intensity of the received two inspection light and measures a state of blood stream in the blood vessel within the living body (herein in the head portion) based on the produced signals. The control unit 90 outputs a starting signal for monitoring the state of blood stream to the living body light measurement apparatus 93 and takes in a signals representing the blood stream state detected by the living body light measurement apparatus 93.

An injector drive unit 94 is for injecting thrombus dissolving agent into the human body with an injection probe 94a depending on the blood stream state detected by the living body light measurement apparatus 93. Since the injection of the thrombus dissolving agent may increase a danger of hemorrhagic adverse effect at the outside of the infarction portion, the injection amount thereof should be strictly controlled. In the present embodiment, the injection amount of the thrombus dissolving agent is controlled by the control unit 90.

On a monitor 95, respective operating conditions of the thrombus detection unit 91, the ultrasonic wave transmission unit 92, the living body light measurement apparatus 93 and the injector drive unit 94 are displayed. In the drawing, as an example of the monitor 95 a monitor image 95a is displayed. The monitor image 95a is constituted such as by a thrombus monitor, an ultrasonic wave irradiation monitor, a living body light measurement image and a dissolving agent monitor. On the thrombus monitor, such as a total number of thrombi having a size larger than a predetermined size detected by the thrombus detection unit 91 and a graph showing detection frequency along time as abscissa are displayed. On the ultrasonic wave irradiation monitor, such as a characteristic value and irradiation time of treatment use ultrasonic waves are displayed. On the living body light measurement image, such as an image illustrating a blood stream state in a blood vessel measured by the living body light measurement apparatus is displayed. On the dissolving agent monitor, such as an amount of dissolving agent injected and the injection time are displayed.

Figure 10:
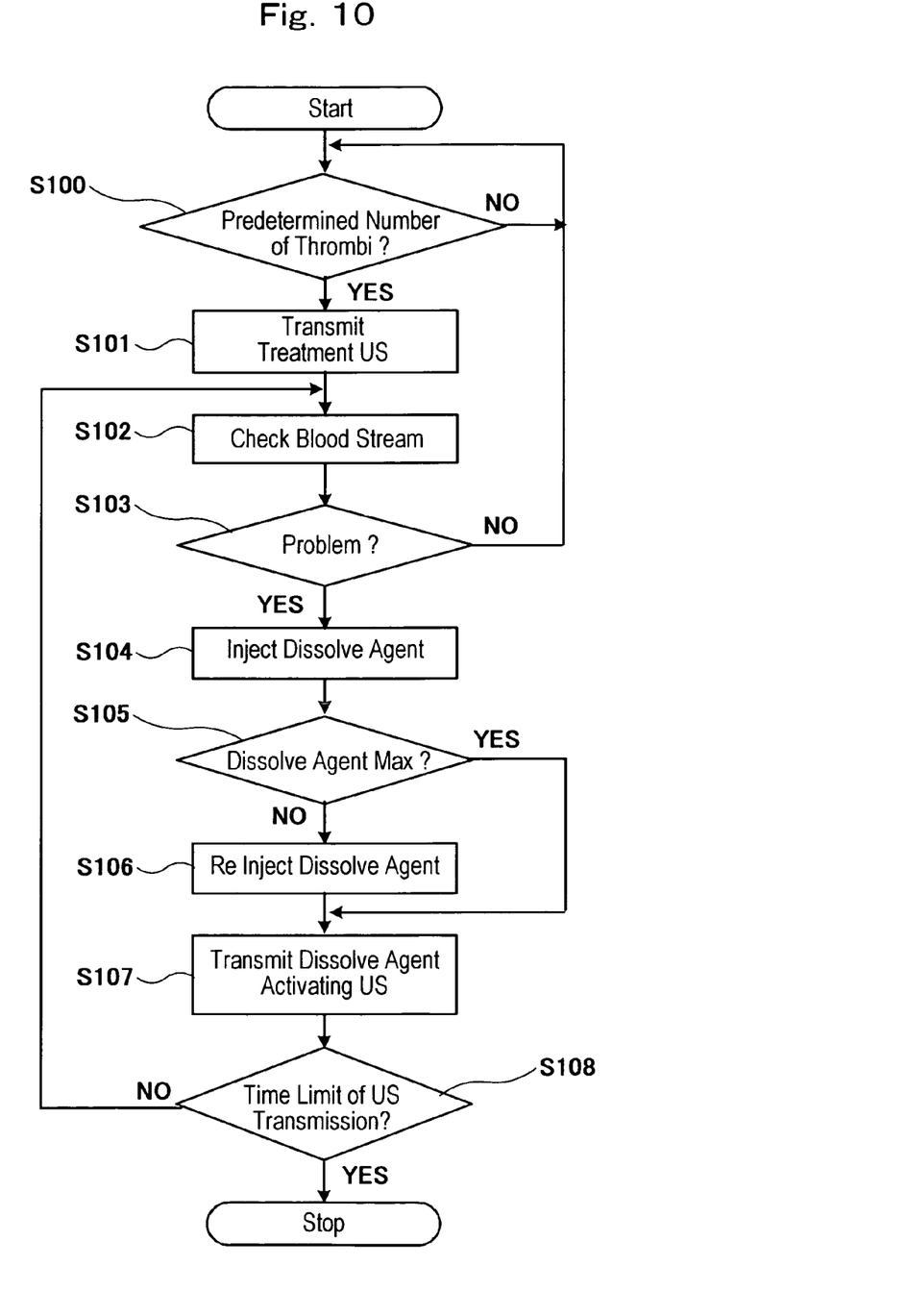
FIG. 10 is a flowchart showing an operation example of the thrombus treating apparatus as shown in FIG. 9.

FIG. 10 is a flowchart showing an operation example of the thrombus treating apparatus as shown in FIG. 9. Herein below, the operation of the thrombus treating apparatus will be explained according to the step order. In step S100, it is judged whether a predetermined number of thrombi flowing through the blood vessel is detected by the thrombus detection unit 91 and when judged detected (YES), the process advances to step S101 and when (NO), the process is repeatedly executed until the predetermined number of thrombi is detected. In step S101, since the predetermined number of thrombi is detected by the thrombus detection unit 91, a thrombus treatment starting signal is sent out to the ultrasonic wave transmission unit 92, drive pulses are supplied to the treatment use transducers 92a and 92b and treatment use ultrasonic waves are transmitted to the head portion. In step S102, a state of blood stream in a blood vessel inside the living body (head portion) is measured by the living body light measurement apparatus 93. In step S103, it is judged whether the result of blood stream check by the living body light measurement apparatus 93 is problematic and when judged problematic (YES), the process advances to the subsequent step S104 and a predetermined amount of thrombus dissolving agent is injected, and when judged no problematic (NO) the process returns to S100. In step S105, it is judged whether the amount of thrombus agent already injected by the injector drive unit 94 reaches the maximum value and when judged reached (YES), the process jumps to step S107 and when judged not yet reached (NO), the process advances to the subsequent step S106. In step S106, the dissolving agent is injected again by the injector drive unit 94. In step S107, in association with the injection of the dissolving agent and in order to activate the dissolving agent, the drive pulses are supplied to the treatment use transducers 92a and 92b from the ultrasonic wave transmission unit 92, and for example, ultrasonic waves having frequency of 20 [kHz]~2 [MHz] and intensity of 0.1~1.0 [W/cm$^2$] are transmitted. In step S108, it is judged whether the transmission time of the treatment use ultrasonic waves as well as the dissolving agent activation use ultrasonic waves is reached to the limit, and when judged not reached (NO), the process returns to step S102 and when judged reached (YES), the treatment finishes.

In FIG. 9 embodiment, although the example in which the treatment use transducer serving also as the thrombus dissolving agent activation use transducer is attached to the head portion, a treatment use transducer which outputs thrombus dissolving use ultrasonic waves can be separately provided near the detection use transducer 10. Then, the transmission of the treatment use ultrasonic waves in step S101 can be performed by the separately provided treatment use transducer or by both treatment use transducers.

The invention claimed is:

1. A thrombus detecting apparatus comprising:
    a transducer, which is attached to a monitor portion of a subject and transmits and receives ultrasonic waves, a transmitter and receiver unit, which transmits and applies driving pulses to the transducer and receives echo signals output from the transducer, and
    a first detector which processes output signals of the transmitter and receiver unit, and detects a thrombus passing through a blood vessel, and
    a light source, which generates living body inspection light,
    a probe, which is attached to a monitor portion of the subject and irradiates the living body inspection light from the light source to the subject,
    a light receiving unit, which receives living body inspection light irradiated from the probe and passed through the subject and outputs electrical signals depending on the intensity of the received living body inspection light, and
    a second detector which processes the output signals of the light receiving unit and detects a thrombus passing through a blood vessel,
    characterized in further comprising a thrombus comprising a thrombus counting unit, which counts both the number of thrombus detected by the first detector and the number of thrombus detected by the second detector.

2. A thrombus detecting apparatus according to claim 1, characterized in further comprising an alarm device, which generates an alarm based on the number of thrombus counted by the thrombus counting unit.

3. The thrombus detecting apparatus according to claim 2, wherein:
    the number of thrombus counted by the thrombus counting unit results from addition of the number of thrombus detected by the first detector and the number of thrombus detected by the second detector; and
    the alarm device generates the alarm if the number of thrombus counted by the thrombus counting unit exceeds a threshold value.

4. The thrombus detecting apparatus according to claim 2, wherein:
    the thrombus counting unit independently counts the number of thrombus detected by the first detector and the number of thrombus detected by the second detector; and
    the alarm device generates the alarm if the number of thrombus counted by the thrombus counting unit for either the first detector or the second detector exceeds a threshold value.

5. The thrombus detecting apparatus according to claim 4, wherein the threshold value includes a first value applied to the first detector, and a second threshold value applied to the second detector.

6. A thrombus detecting apparatus according to claim 1 or 2, characterized in that the thrombus detecting apparatus further comprising a portable self power source.

7. A thrombus treating apparatus comprising:
a transducer, which is attached to a monitor portion of a subject and transmits and receives ultrasonic waves,
a transmitter and receiver unit, which transmits and applies driving pulses to the transducer and receives echo signals output from the transducer, and
a first detector which processes output signals of the transmitter and receiver unit, and detects a thrombus passing through a blood vessel, and
a light source, which generates living body inspection light,
a probe, which is attached to a monitor portion of the subject and irradiates the living body inspection light from the light source to the subject,
a light receiving unit, which receives living body inspection light irradiated from the probe and passed through the subject and outputs electrical signals depending on the intensity of the received living body inspection light,
a second detector which processes the output signals of the light receiving unit and detects a thrombus passing through a blood vessel,
characterized in further comprising a thrombus counting unit, which counts the number of thrombus by adding the number of thrombus detected by the first detector and the number of thrombus detected by the second detector, and
a treatment use ultrasonic wave generating device, which transmits ultrasonic waves for dissolving a thrombus flowing through the blood vessel based on the counted number of the thrombus.

8. A thrombus treating apparatus according to claim 7, characterized in that the thrombus treating apparatus further comprising:
a living body light measurement apparatus, which observably displays a state of blood stream in the blood vessel, and
an injection device, which injects thrombus dissolving agent into the blood vessel depending on the state of blood stream in the blood vessel observed by the living body light measurement apparatus.

9. A thrombus treating apparatus according to claim 8, characterized in that the thrombus treating apparatus further comprising:
a control device, which monitors the injection amount of the thrombus dissolving agent by the injection device and the transmission time of the ultrasonic waves by the treatment use ultrasonic generating device and adjusts and controls the injection amount and the irradiation time.

10. A thrombus treating apparatus according to claim 9, characterized in that the thrombus treating apparatus further comprising:
a thrombus dissolving agent activation use ultrasonic wave generating device, which transmits ultrasonic waves for activating the thrombus dissolving agent injected into the blood vessel from the injection device attached to the subject.

11. A thrombus detecting method comprising:
a step of transmitting and irradiating ultrasonic waves and living body inspection light from an ultrasonic wave transducer and a living body light measurement probe attached at a monitor portion of a subject toward a blood vessel at the monitor portion,
a step of measuring echo signals and/or penetrating living body light from the blood vessel at the monitor portion, and
a step of counting a number of thrombus flowing in the blood vessel at the monitor portion based on addition of the intensity of the measured echo signals and penetrating living body light.

12. A thrombus detecting method according to claim 11 further comprising:
a step of generating an alarm when the thrombus detection number in the counting step reaches a predetermined number.

13. A thrombus treating method comprising:
a step of transmitting and irradiating ultrasonic waves and living body inspection light from an ultrasonic wave transducer and living body inspection light from an ultrasonic wave transducer and a living body light measurement probe attached at a monitor portion of a subject toward a blood vessel at the monitor portion,
a step of measuring echo signals and penetrating living body light from the blood vessel at the monitor portion,
a step of counting a number of thrombus flowing in the blood vessel at the monitor portion based on addition of the intensity of the measured echo signals and penetrating living body light, and
a step of transmitting treatment use ultrasonic waves toward the blood vessel from the treatment use transducer attached to the subject for dissolving a thrombus passing through the blood vessel when a thrombus is counted in the counting step.

14. A thrombus treating method according to claim 13 further comprising:
a step of observing and displaying a state of blood stream in the blood vessel by attaching a living body light measurement apparatus to the subject,
a step of injecting a thrombus dissolving agent into the blood vessel depending on the observed and displayed state of blood stream in the blood vessel.

15. A thrombus treating method according to claim 14 further comprising:
a step of monitoring the transmission time of the treatment use ultrasonic waves and the injection amount of the thrombus dissolving agent and interrupting the transmission of the treatment use ultrasonic waves and the injection of the thrombus dissolving agent when a predetermined transmission time and a predetermined amount are reached.

16. A thrombus treating method according to claim 15 further comprising:
a step of transmitting thrombus dissolving agent activation use ultrasonic waves for activating the injected thrombus agent toward the blood vessel.

* * * * *